(12) United States Patent
Olah

(10) Patent No.: US 7,038,099 B2
(45) Date of Patent: May 2, 2006

(54) ENVIRONMENTALLY SAFE ALKYLATION OF ALIPHATIC AND AROMATIC HYDROCARBONS WITH OLEFINS USING SOLID HF-EQUIVALENT CATALYSTS

(76) Inventor: George A Olah, 2252 Gloaming Way, Beverly Hills, CA (US) 90210

( * ) Notice: Subject to any disclaimer, the term of this patent is extended or adjusted under 35 U.S.C. 154(b) by 80 days.

(21) Appl. No.: 10/721,896

(22) Filed: Nov. 26, 2003

(65) Prior Publication Data

US 2004/0138513 A1     Jul. 15, 2004

Related U.S. Application Data

(62) Division of application No. 09/858,584, filed on May 17, 2001, now Pat. No. 6,677,269.

(51) Int. Cl.
*C07C 2/68* (2006.01)
*C07C 2/60* (2006.01)

(52) U.S. Cl. ............... 585/456; 585/462; 585/464; 585/723; 585/724

(58) Field of Classification Search ............... 585/456, 585/462, 464, 723, 724
See application file for complete search history.

(56) References Cited

U.S. PATENT DOCUMENTS

| | | |
|---|---|---|
| 5,073,674 A | 12/1991 | Olah |
| 5,118,804 A | 6/1992 | Defaye et al. |
| 5,663,474 A | 9/1997 | Pham et al. |
| 6,177,058 B1 | 1/2001 | Singh et al. |
| 6,200,924 B1 | 3/2001 | Lloyd et al. |
| 6,281,309 B1 | 8/2001 | Babcock et al. |
| 6,395,673 B1 | 5/2002 | Harmer et al. |

*Primary Examiner*—Thuan D Dang
(74) *Attorney, Agent, or Firm*—Jones Day

(57) ABSTRACT

A method of alkylating aliphatic or aromatic hydrocarbons with olefins using solid hydrogen fluoride-equivalent catalysts is described. Preferred catalysts comprise solid polymeric onium polyhydrogen fluoride complexes.

21 Claims, No Drawings

ENVIRONMENTALLY SAFE ALKYLATION OF ALIPHATIC AND AROMATIC HYDROCARBONS WITH OLEFINS USING SOLID HF-EQUIVALENT CATALYSTS

CROSS-REFERENCE TO RELATED APPLICATIONS

This application is a divisional of U.S. application Ser. No. 09/858,584, filed May 17, 2001, now U.S. Pat. No. 6,677,269 the entirety of which is incorporated herein by reference.

FIELD OF THE INVENTION

The present invention relates to a method for alkylating aliphatic or aromatic hydrocarbons with olefins using solid hydrogen fluoride-equivalent catalysts. The process is environmentally safe and represents improved and simplified technology easily adaptable to presently operating commercial hydrogen fluoride alkylation plants.

BACKGROUND OF THE INVENTION

Anhydrous hydrogen fluoride is widely used as a catalyst in the petrochemical industry. It is particularly effective as alkylation catalyst, such as in the production of high-octane gasoline via isoalkane-olefin alkylation. Similarly, detergent alkylates are produced by alkylating aromatic compounds, such as benzene. These technologies have achieved significant application in industry. At the same time, because of the volatility of hydrogen fluoride (HF; boiling point of about 19.6° C.), the environmental and health dangers posed by accidental release from industrial reactors or storage tanks is increasingly unacceptable. To solve this problem, industry has reverted either to the use of sulfuric acid, a less suitable but also less volatile alkylation catalyst, or has operated in a manner that decreases or minimizes the volatility of hydrogen fluoride.

For example, U.S. Pat. No. 5,073,674 discloses the utility of liquid onium polyhydrogen fluoride complexes, containing about 70% to 95% by weight of hydrogen fluoride, as alkylation catalysts. These liquid catalysts, which are not polymer-based, typically have a relatively low molecular weight, optionally contain an additional Lewis acid halide or strong Bronstead acid co-catalyst.

Certain polyhydrogen fluoride complexes, such as polyhydrogen fluoride complexes of pyridine and its derivatives, are liquids which are used as fluorinating agents. For example, anhydrous hydrogen fluoride in the presence of pyridine has been used for fluorinating steroids (R. R. Hirschmann et al., *J. Am. Chem. Soc.*, 1956, 78, 4956). The 30% pyridine-70% hydrogen fluoride system (PPHF) was found to be particularly useful for this reaction (C. G. Bergstrom et al., *J. Org. Chem.*, 1963, 28, 2633) and subsequently was developed (Olah et al., *J. Org. Chem.*, 1979, 44, 3872, and references cited therein) as a general fluorinating agent. The PPHF reagent and subsequently developed related reagents (T. Fukuhara et al., *Nippon Kagaku Kaish.*, 1985, p. 1951) are, however, only suitable as convenient fluorinating agents and are not catalysts for alkylation.

Solid poly-4-vinylpyridinium polyhydrogen fluoride has also previously been utilized for fluorination (Olah et al., *Synthesis*, 1993, p. 693). This solid fluorination agent, which contains only 35% to 60% hydrogen fluoride by weight is not effective as an alkylation catalyst. Acidic metal hydrogen fluorides, such as those of the type $M^+HF_2^-$, as well as most other salts of hydrogen fluoride, also fail to catalyze the alkylation of hydrocarbons.

SUMMARY OF THE INVENTION

This invention is based, in part, on the discovery that certain solid polymeric onium polyhydrogen fluoride complexes can be used to catalyze or facilitate the alkylation of aliphatic or aromatic hydrocarbons with olefins.

One embodiment of the invention relates to a method of alkylating an aliphatic or aromatic hydrocarbon with an olefin, which comprises contacting the aliphatic or aromatic hydrocarbon with the olefin in the presence of a solid polymeric onium polyhydrogen fluoride complex under conditions sufficient for the alkylation of the aliphatic or aromatic hydrocarbon.

Advantageously, polymeric onium polyhydrogen fluoride complexes used in the invention are solid. In a preferred embodiment, the polymeric onium polyhydrogen fluoride complex contains from about 70% to 95% by weight hydrogen fluoride. In another preferred embodiment, the polymeric onium polyhydrogen fluoride complex contains in some or all of its repeat units a nitrogen, phosphorus, or sulfur atom capable of forming an onium fluoride moiety upon reaction or complexation with hydrogen fluoride.

In another embodiment, the method may further comprise contacting the aliphatic or aromatic hydrocarbon and the olefin with a Lewis acid halide or a strong Bronstead acid. When added, the co-catalyst is preferably present in an amount from about 0.1% to 10% by weight of the polymeric onium polyhydrogen fluoride complex.

Another embodiment of the present invention relates to a process for forming a solid polymeric onium polyhydrogen fluoride complex, which comprises contacting a homopolymer or copolymer including, in at least one repeat unit, an atom, preferably nitrogen, phosphorus, or sulfur, capable of forming an onium fluoride moiety upon reaction or complexation with a source of hydrogen fluoride, preferably anhydrous hydrogen fluoride, under conditions sufficient to form the solid polymeric onium polyhydrogen fluoride complex.

Still another embodiment relates to a process for removing hydrogen fluoride from an alkylation product of the invention by contacting it with a solid homopolymer or copolymer including, in at least one repeat unit, an atom, preferably nitrogen, phosphorus, or sulfur, capable of forming an onium fluoride moiety upon reaction or complexation with a source of hydrogen fluoride, under conditions sufficient for the solid homopolymer or copolymer to complex hydrogen fluoride. In a preferred embodiment, the alkylation process does not necessitate any caustic or aqueous washing steps.

DETAILED DESCRIPTION OF THE PREFERRED EMBODIMENTS

The invention is based on the unexpected discovery that certain environmentally-friendly, solid polymeric onium polyhydrogen fluoride complexes can, in fact, catalyze the alkylation of aliphatic or aromatic hydrocarbons with olefins.

As used herein, the term "solid polymeric onium polyhydrogen fluoride complex" refers to any solid polymeric or oligomeric material containing in some or all of its repeat units an atom, preferably nitrogen, phosphorus, or sulfur, more preferably nitrogen, capable of forming an onium (e.g., preferably ammonium, phosphonium, or sulfonium) fluoride moiety with hydrogen fluoride. Suitable solid polymeric onium polyhydrogen fluoride complexes include, but are not limited to, complexes and/or reaction products of hydrogen fluoride and polymers such as, but not limited to, poly (vinylpyridine) and poly(aminomethyl styrene), as shown below:

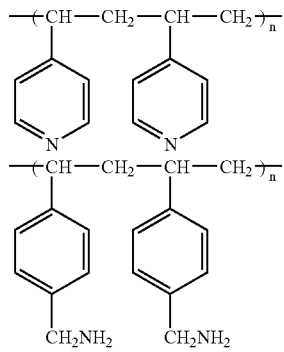

as well as mixtures or copolymers containing same, wherein "n" denotes the number of repeat units. With appropriate amounts of anhydrous hydrogen fluoride, the polymers or oligomers can form corresponding stable poly(hydrogen fluoride) salts. Examples of the prepared solid polyhydrogen fluoride complexes include, but are not limited to, polyvinylpyridinium polyhydrogen fluoride (PVPHF) or poly(4-aminomethyl)styryl polyhydrogen fluoride (PAMSHF), as shown below:

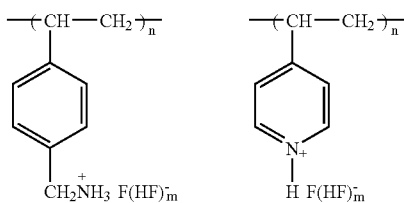

as well as mixtures or copolymers containing same, wherein m is such that the resultant polymeric onium polyhydrogen fluoride complex can catalyze an alkylation reaction. The range of values for m for each polymeric onium polyhydrogen fluoride complex may depend on the repeat unit weight of the non-complexed polymers, and is preferably such that the solid polymeric onium polyhydrogen fluoride complex contains from about 70 to about 95 weight percent hydrogen fluoride, with the polymeric component being present in an amount from about 30 to about 5 weight percent. For example, m can be from about 5 to about 200, or from about 10 to about 100. The solid polymeric onium polyhydrogen fluoride complexes thus formed can serve as solid equivalents of anhydrous hydrogen fluoride, facilitating alkylation reactions at their surfaces and/or providing hydrogen fluoride in low concentrations to hydrocarbons with which they come in contact.

The use of solid polymeric onium polyhydrogen fluoride complexes to effect alkylation has other significant advantages. For example, their reduced volatility reduces accidental atmospheric release of gaseous hydrogen fluoride. The polymeric onium polyhydrogen fluoride complexes can also be efficiently diluted with water and neutralized with caustic treatment, without forming dangerous aerosols characteristic of gaseous hydrogen fluoride release. Also, because of their low vapor pressure (e.g., below about 50° C.), the operating pressures in alkylation reactors and storage tanks can be substantially decreased.

A first embodiment of the invention encompasses a method of alkylating an aliphatic or aromatic hydrocarbon which includes contacting the aliphatic or aromatic hydrocarbon with an olefin in the presence of a solid polymeric onium polyhydrogen fluoride complex under conditions sufficient for the alkylation of the aliphatic or aromatic hydrocarbon. As used herein, the term "aliphatic hydrocarbon" encompasses saturated hydrocarbons, preferably isoalkanes. Isoalkanes according to the invention preferably contain from about 4 to about 10 carbon atoms ($C_4$–$C_{10}$). As used herein, the term "aromatic hydrocarbon" encompasses poly- and mono-cyclic aromatic hydrocarbons, such as benzene. Aromatic hydrocarbons according to the invention preferably contain from about 6 to about 20 carbon atoms ($C_6$–$C_{20}$). In one method of this embodiment, the reaction product is a high-octane alkylate. In another method, the reaction product is a detergent alkylate.

Examples of olefins used in alkylating aliphatic hydrocarbons include, but are not limited to, ones that contain from three to eight carbon atoms ($C_3$–$C_8$), and preferentially ones that contain from four to six carbon atoms ($C_4$–$C_6$). Examples of olefins used in alkylating aromatic hydrocarbons include, but are not limited to, ones that contain from about two to about twenty carbon atoms ($C_2$–$C_{20}$).

In a preferred method, the alkylation reaction is conducted at a temperature of from about 0° C. to about 50° C. and at a pressure of from about atmospheric to about 800 psi. Advantageously, the alkylation reaction can be conducted batchwise or under continuous flow conditions, with an aliphatic or aromatic hydrocarbon to olefin molar ratio of from about 2:1 to about 20:1. Under batchwise conditions, higher yields can be obtained by adding the olefin in portions to the aliphatic or aromatic hydrocarbon to be alkylated and the solid polymeric onium polyhydrogen fluoride complex. Under flow conditions, the olefin and the aliphatic or aromatic hydrocarbon to be alkylated, in the proper ratios, are passed through solid polymeric onium polyhydrogen fluoride resins.

In specific methods of the invention, improved yields can be obtained by adding a co-catalyst to the reaction mixture in an amount of about 0.1 to about 10 weight percent of the hydrogen fluoride contained in the solid polymeric onium polyhydrogen fluoride complex being used. Examples of co-catalysts include, but are not limited to, Lewis acid halides such as boron tristriflate, strong Bronstead acids such as fluorosulfuric or perfluoroalkanesulfonic acid, and mixtures thereof.

In a preferred method of the invention, a saturated, branched, aliphatic hydrocarbon, e.g., isobutane, is alkylated with an olefin, e.g., isobutylene, in the presence of a solid polymeric onium polyhydrogen fluoride complex at a temperature of from about 0° C. to about 50° C. and a pressure of from about atmospheric to about 800 psi for a time sufficient to form a high-octane alkylate. In another preferred method, an aromatic hydrocarbon, e.g., benzene, is alkylated with an olefin, e.g., dodecene, to form a detergent alkylate, e.g., dodecylbenzene, which upon sulfonation under sufficient conditions can yield a widely used detergent.

Preferably, alkylation reactions according to the invention include reaction of an isoalkane with an olefin to give high-octane alkylate products. Examples of high-octane alkylate products have from about 6 to about 12 carbons ($C_6$–$C_{12}$) and can be useful or present in gasoline. In a particularly preferred method, isobutane or isopentane is reacted with a $C_4$–$C_5$ olefin, such as isobutylene. Alkylation of aromatic hydrocarbons, such as benzene, with liquid olefins having about 10 to about 20 carbon atoms ($C_{10}$–$C_{20}$) can result in detergent alkylates. Whereas these reactions are presently practiced commercially using anhydrous hydrogen fluoride, the present invention can particularly minimize or eliminate environmental and health hazards associated with the use of volatile and toxic anhydrous hydrogen fluoride in industrial alkylation plants. The polymers used in the invention can immobilize volatile anhydrous hydrogen fluoride by reacting therewith to form solid polymeric onium polyhydrogen fluoride complexes. Thus the resulting complexes exhibit substantially decreased volatility and aerosol formation compared to highly toxic hydrogen fluoride in case of accidental release to the atmosphere.

Methods of the invention are readily adaptable to use in existing plant equipment. Their industrial use should not involve costly process changes or major changes in operating technology. One particular further practical advantage of the invention is that the processing of the alkylate reaction products can be performed in a greatly simplified and low cost way.

The invention optionally provides that the alkylates can be treated without any washing or caustic solution, e.g., by passing the alkylates through a bed or column filled with a fresh basic polymer, e.g., PVP or PAMS. These basic polymers can remove hydrogen fluoride from the alkylates through complexation to form the corresponding solid polymeric onium polyhydrogen fluoride salts. In this way, hydrogen fluoride removal and solid polymeric onium polyhydrogen fluoride complex regeneration can be achieved simultaneously.

EXAMPLES

The following are examples of methods and materials which can be used according to the present invention, and are not to be construed as limiting the scope of the invention in any way.

Example 1

A solid polymeric polyhydrogen fluoride catalyst was prepared by placing 19.5 g of poly (4-vinylpyridine) (PVP, approximately 2% crosslinked) into a polyethylene bottle, cooling it to about −78° C., and adding about 80.5 g of anhydrous hydrogen fluoride in small portions, thus forming the poly (4-vinylpyridinium) polyhydrogen fluoride (PVPHF) catalyst.

After warming to room temperature, the PVPHF catalyst was then added into a 600 mL, mechanically stirred stainless steel or Monel autoclave, to which then about 220 mL of liquid isobutane and about 20 mL of isobutylene was fed. The reactor was stirred while keeping the temperature at about 35° C. to 40° C. for about 30 minutes. The reactor was cooled with ice water and depressurized by venting of excess isobutane. The alkylate product of the isobutane-isobutylene reaction was then passed through a column containing fresh PVP to absorb any excess HF. The alkylate product was distilled and analyzed by GC-MS (a gas chromatography apparatus coupled to a mass spectrometer). It gave approximately a 70% yield with a research octane number (RON) of about 90. Of that yield, the alkylate product was found to contain about 63% of octane isomers, with 2,2,4-trimethylpentane (TMP) amounting to 36% of the alkylate product. The Cg and higher alkylate fractions amounted to about 10–14% of the product.

Example 2

The isobutane-isobutylene alkylation reaction was carried out as in Example 1, but poly (4-aminomethyl styrene) (PAMS) was substituted for PVP. The catalyst reaction of Example 2 involved a similar ratio of amino groups to anhydrous hydrogen fluoride added as in Example 1. A 65% yield of alkylate product was obtained with a RON of about 91.5. Of that yield, the alkylate product was found to contain about 42% 2,2,4-TMP. The $C_9$ and higher alkylate fractions amounted to about 10–16% of the product.

Example 3

The isobutane-isobutylene alkylation reaction was carried out as in Example 2, except that the isobutylene was incrementally fed in small portions to the reactor containing the isobutane and the polymeric onium polyhydrogen fluoride catalyst. The alkylate product obtained in this manner generally contained less than about 10% of $C_9$ and higher alkylate fractions.

Examples 4–5

For Examples 4–5, each polymeric onium polyhydrogen fluoride catalyst, as prepared in Examples 1–2, respectively, was loaded in to a reaction vessel, along with about 200 mL benzene and about 40 mL of a liquid olefin having from about 12 to 18 carbons (or a mixture of olefins obtained by dehydrogenation of a corresponding $C_{12}$ to $C_{18}$ alkane mixture). The reaction vessel was stirred at about 60° C. to 70° C. for about 1 hour. After removal of hydrogen fluoride from the alkylate by treatment with the corresponding fresh basic polymer, the corresponding detergent alkylates were obtained in approximately 85% to 90% yield.

The embodiments of the invention described above are intended to be merely exemplary, and those skilled in the art will recognize, or will be able to ascertain using no more than routine experimentation, numerous equivalents of the specific materials and procedures described herein. All such equivalents are considered to be within the scope of the invention and are encompassed by the appended claims.

What is claimed is:

1. A method of alkylating an aliphatic or aromatic hydrocarbon with an olefin, which comprises contacting the aliphatic or aromatic hydrocarbon with the olefin in the presence of a solid polymeric onium polyhydrogen fluoride complex under conditions sufficient for the alkylation of the aliphatic or aromatic hydrocarbon.

2. The method of claim 1, wherein the aliphatic hydrocarbon is a $C_4$–$C_{10}$ saturated, branched hydrocarbon.

3. The method of claim 2, wherein the olefin is a $C_2$–$C_8$ alkene.

4. The method of claim 3, wherein the alkylation of the aliphatic hydrocarbon produces a high-octane $C_6$–$C_{12}$ branched alkane.

5. The method of claim 3, wherein the molar ratio of the saturated, branched hydrocarbon to the olefin ranges from about 2:1 to about 20:1.

6. The method of claim 1, wherein the aromatic hydrocarbon is a $C_6$–$C_{20}$ aromatic hydrocarbon.

7. The method of claim 6, wherein the olefin is a $C_2$–$C_{20}$ alkene.

8. The method of claim 7, wherein the alkylation of the aromatic hydrocarbon produces a detergent alkylate.

9. The method of claim 8, wherein the detergent alkylate is further sulfonated under conditions sufficient to produce a detergent.

10. The method of claim 1, wherein the solid polymeric onium polyhydrogen fluoride complex comprises a polymeric material containing in some or all of its repeat units a nitrogen, phosphorus, or sulfur atom capable of forming an onium fluoride moiety upon reaction or complexation with anhydrous hydrogen fluoride.

11. The method of claim 1, wherein the solid polymeric onium polyhydrogen fluoride component comprises from about 70 to about 95 weight percent hydrogen fluoride.

12. The method of claim 1, which further comprises contacting the aliphatic or aromatic hydrocarbon with the olefin in the presence of a Lewis acid halide or a strong Bronstead acid.

13. The method of claim 12, wherein the Lewis acid halide or strong Bronstead acid is present in an amount from about 0.1 to about 10 weight percent of the solid polymeric onium polyhydrogen fluoride complex.

14. A method of alkylating an aliphatic or aromatic hydrocarbon with an olefin, which comprises contacting the aliphatic or aromatic hydrocarbon with the olefin in the presence of a solid polymeric onium polyhydrogen fluoride complex under conditions sufficient for the alkylation of the aliphatic or aromatic hydrocarbon, wherein the solid polymeric onium polyhydrogen fluoride complex is poly(vinylpyridinium) polyhydrogen fluoride or poly(aminomethyl)styryl polyhydrogen fluoride.

15. The method of claim 14, wherein the aliphatic hydrocarbon is a $C_4$–$C_{10}$ saturated, branched hydrocarbon.

16. The method of claim 15, wherein the olefin is a $C_2$–$C_8$ alkene.

17. The method of claim 16, wherein the alkylation of the aliphatic hydrocarbon produces a high-octane $C_6$–$C_{12}$ branched alkane.

18. The method of claim 16, wherein the molar ratio of the saturated, branched hydrocarbon to the olefin ranges from about 2:1 to about 20:1.

19. The method of claim 14, wherein the aromatic hydrocarbon is a $C_6$–$C_{20}$ aromatic hydrocarbon.

20. The method of claim 19, wherein the olefin is a $C_2$–$C_{20}$ alkene.

21. The method of claim 20, wherein the alkylation of the aromatic hydrocarbon produces a detergent alkylate which is further sulfonated under conditions sufficient to produce a detergent.

* * * * *